(12) United States Patent
Li

(10) Patent No.: US 9,327,251 B2
(45) Date of Patent: May 3, 2016

(54) SYSTEM AND METHOD FOR IMPROVED GAS DISSOLUTION

(71) Applicant: LanzaTech New Zealand Limited, Auckland (NZ)

(72) Inventor: Xueliang Li, Auckland (NZ)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 0 days.

(21) Appl. No.: 14/166,567

(22) Filed: Jan. 28, 2014

(65) Prior Publication Data

US 2014/0212937 A1    Jul. 31, 2014

Related U.S. Application Data

(60) Provisional application No. 61/757,851, filed on Jan. 29, 2013.

(51) Int. Cl.
| | | |
|---|---|---|
| *C12P 7/56* | (2006.01) | |
| *B28C 5/06* | (2006.01) | |
| *B01F 3/04* | (2006.01) | |
| *B01F 13/10* | (2006.01) | |
| *C12M 1/00* | (2006.01) | |

(52) U.S. Cl.
CPC ......... *B01F 3/04496* (2013.01); *B01F 3/04262* (2013.01); *B01F 3/04751* (2013.01); *B01F 3/04985* (2013.01); *B01F 13/1022* (2013.01); *C12M 29/04* (2013.01); *C12M 29/06* (2013.01)

(58) Field of Classification Search
None
See application file for complete search history.

(56) References Cited

U.S. PATENT DOCUMENTS

| | | | |
|---|---|---|---|
| 4,336,224 A * | 6/1982 | Siposs | 422/46 |
| 4,938,865 A | 7/1990 | Jameson | |
| 5,173,429 A | 12/1992 | Gaddy et al. | |
| 5,593,886 A | 1/1997 | Gaddy | |
| 5,951,875 A | 9/1999 | Kanel et al. | |
| 6,368,819 B1 | 4/2002 | Gaddy et al. | |
| 8,143,037 B2 | 3/2012 | Zahn et al. | |
| 2009/0035848 A1 | 2/2009 | Hickey | |

FOREIGN PATENT DOCUMENTS

| | | |
|---|---|---|
| AU | 677542 | 2/1996 |
| WO | WO02/08438 | 1/2002 |
| WO | WO2008/115080 | 9/2008 |
| WO | WO2009/064200 | 5/2009 |

OTHER PUBLICATIONS

Terasaka et al., Chemical Engineering Science, 2011, vol. 66, p. 3172-3179.*
Abrini, J. Naveau, H. & Nyns, E.J., Archives of Microbiology, (1994), 161, 345-351.
Bredwell et al., Mass Transfer Properties of Microbubbles, Part 1: Experimental Studies, Biotechnol. Prog., (1998), 14, 31-38.
Kopke, Michael et al., 2,3 butanediol production by acetogenic bacteria, an alternativeroute to chemical synthesis, using industrial waste gas, Appln. Environ. Microbiol., 17, Jun. 2011, vol. 77, No. 15, pp. 5467-5475.
Tanner, R.S. Miller, L.M., & Yang, D., International Journal of Systematic Bacteriology, (1993), 43, 232-236.
Tirado-Acevedo O., Production of Bioethanol from Synthesis Gas Using Clostridium Ijungdahlii. PhD thesis, North Carolina State University, 2010.
Tyurin, M. & Kiriukhin, M., Electrofusion of cells of *Acetogen clostridium* sp. MT 351 with erm(B) or cat in the chromosome, Journal of Biotech Research, (2012), 4:1-12.1-12.
PCT Search Report (PCT/NZ2014/00009) dated Aug. 7, 2014.

\* cited by examiner

*Primary Examiner* — Kade Ariani
(74) *Attorney, Agent, or Firm* — Frank S Molinaro

(57) ABSTRACT

The invention provides a microbubble generation system with increased efficiency and flexibility compared to known systems. Further, the invention provides a method of microbubble generation. In particular, invention relates to increasing the efficiency of a fermentation reaction by reducing bubble size and increasing gas absorption into a liquid fermentation broth.

18 Claims, 6 Drawing Sheets

SYSTEM AND METHOD FOR IMPROVED GAS DISSOLUTION

FIELD OF INVENTION

The invention relates to a system for reducing gas bubble size in a liquid and associated methods of use. More particularly, the invention relates to increasing the efficiency of a fermentation reaction by reducing bubble size and increasing gas absorption into a liquid fermentation broth.

BACKGROUND

A number of processes utilise gas dissolved in a liquid substrate. In order to maximise the dissolution of gas into the liquid, the gas bubble surface area should be maximised. This can be achieved by minimising the bubble size.

There are known methods and apparatus for producing these "microbubbles", such as those described in U.S. Pat. No. 4,938,865 and AU677542. The apparatus described in these documents is known as the Jameson cell and facilitates the introduction of gas to a liquid stream to produce a foam layer. The Jameson Cell employs a single plunging jet of liquid to entrain atmospheric air via the Bernoulli effect which breaks it into very small bubbles within a zone of very high shear stress as the jet enters the liquid.

In the Jameson cell, the gas has to be injected at the top of a column and it is entrained by the high speed liquid. To enable gas entrainment to happen, the Jameson cell has a requirement of a minimum jet velocity. This is variously referred to as being 8 m/s or 15 m/s. It would be an advantage to be able to obtain microbubbles at a lower minimum jet velocity to increase energy efficiency of the system and provide increased flexibility by allowing jet velocity to vary based on the requirements of a specific application.

The mechanism of gas entrainment in the Jameson cell requires that the gas inlet orifice and the liquid jet have to be surrounded by a downcomer to generate a suction effect. The Jameson cell also requires a vessel additional to the pipe to receive the liquid jet and the mixture. The Jameson cell is designed for use in the froth flotation of minerals, and specifically promotes small particle attachment in the zone of high shear which causes high rates of viscous dissipation to heat. This requires high turbulence for better contact between mineral particles and gas bubbles. Because of this, the Jameson cell is characterised by its high turbulence in the downcomer. The high turbulence reduces efficiency of the overall system and may harm cells or proteins when used for particular applications such as fermentation by microorganisms.

Fermentation reactions using microorganisms are fed essential substrates in a gaseous form. For example gas streams containing CO and/or $CO_2$ and/or $O_2$ and/or $H_2$ may be pumped into a bioreactor such that they bubble through the fermentation broth and/or may be provided in any headspace in the bioreactor. A portion of the gases in the streams dissolves in the fermentation broth such that it is then usable by the microbes active in the particular reaction. The availability or concentration of the gases in the fermentation broth can have a significant impact on the productivity of fermentation processes. However, gases such as CO and $O_2$ have poor solubility in the generally aqueous broth contained within bioreactors, making it difficult and/or slow to dissolve desired quantities of the gases into the broth for use by the microorganisms in the fermentation process.

A potential method to enhance efficiency of gas fermentations by increasing gas-to-liquid mass-transfer is to sparge with microbubble dispersions. Such an enhancement has been demonstrated for a synthesis-gas fermentation involving *Butyribacterium methylotrophicum* grown in a continuous, stirred-tank reactor using a tangential filter for total cell recycle (Bredwell and Worden 1998, *Biotechnol. Prog.* 14, 31-38).

It is an object of the invention to overcome one or more of the disadvantages of the prior art, or at least to provide the public with a useful choice.

SUMMARY OF THE INVENTION

In a first aspect, the invention provides a microbubble generation system, the system comprising:
 a. a column,
 b. a perforated plate adapted to facilitate introduction of liquid to the column; and
 c. a gas sparger adapted to sparge gas into the column,
wherein the perforated plate is situated above the gas sparger. In use, a portion of liquid flows from the perforated plate and contacts a foam layer produced by sparging of gas into a liquid contained within the column.

In a particular embodiment, the perforated plate substantially fills a cross-section of the column.

In a particular embodiment, the column further comprises a liquid inlet adapted to receive liquid and pass it to the perforated plate.

In a particular embodiment, the column further comprises a gas inlet adapted to receive a gas stream and pass it to the gas sparger.

In a particular embodiment, the column further comprises a liquid outlet adapted to receive a microbubble product generated by the system.

In a particular embodiment, the column further comprises a gas relief valve. Preferably, the gas relief valve is located in the column at a level substantially adjacent and below the level of the perforated plate.

In a particular embodiment, the column comprises an expansion section towards the base of the column whereby the width of the column is increased relative to the width towards the top of the column. In use, this expansion section has the effect of reducing the downward velocity of the liquid and allows more consistent and effective bubble generation via the gas sparger.

In a particular embodiment, the system further comprises a foam/liquid separator adapted to receive a microbubble product from the column.

In a particular embodiment, the foam/liquid separator is adapted to pass at least a portion of a substantially liquid fraction to a liquid inlet on the column, preferably via a liquid pump.

In a particular embodiment, the foam/liquid separator is adapted to pass at least a portion of a substantially foam fraction to a de-foaming tank.

In a particular embodiment, the de-foaming tank comprises an anti-foam spray.

In a particular embodiment, the de-foaming tank is adapted to yield a foamate product for extraction from the system.

In a particular embodiment, the column is a bioreactor for fermentation of a gaseous substrate to produce one or more products. In an alternative embodiment, the bioreactor is connected to the column and the bioreactor is adapted to receive a microbubble product containing microbubbles of the gaseous substrate from the column. In this alternative embodiment, the bioreactor comprises a broth outlet adapted to receive fermentation broth from the bioreactor and pass it to the column.

In a particular embodiment, the microbubble generation system is configured to provide mass transfer of the gaseous substrate to one or more micro-organisms in the fermentation broth.

In a particular embodiment, the bioreactor contains a fermentation broth comprising a culture of one or more carboxydotrophic microorganisms capable of producing one or more products by fermentation of a microbubble product containing CO.

In a particular embodiment, the system further comprises a primary gas-liquid separator adapted to receive fermentation broth from the bioreactor. In particular embodiments, the primary gas-liquid separator is further adapted to pass at least a portion of a substantially gas component of the broth to the column via a compressor/blower and the gas sparger. In a further embodiment, the primary gas-liquid separator is adapted to remove at least a portion of a substantially gas component of the broth from the system.

In a particular embodiment, the primary gas-liquid separator further comprises an anti-foam spray.

In a particular embodiment, the primary gas-liquid separator is adapted to pass at least a portion of the broth to a secondary gas-liquid separator, and/or to pass at least a portion of the broth to a product withdrawal outlet for product extraction.

In a particular embodiment, the secondary gas-liquid separator is adapted to receive fresh media and/or pass at least a portion of the broth to the liquid inlet on the column, preferably via a liquid pump. The secondary gas-liquid separator optionally comprises a gas outlet to remove at least a portion of gas separated from the broth.

In a particular embodiment, the microbubble generation system is part of a microbubble gas absorption system.

In a particular embodiment, the system further comprises a gas-liquid separator adapted to receive a microbubble product from the column.

In a particular embodiment, the gas-liquid separator is adapted to remove at least a portion of a substantially gas component of the microbubble product from the system.

In a particular embodiment, the gas-liquid separator is adapted to pass at least a portion of a substantially liquid portion of the microbubble product to the column, preferably via a liquid pump.

In a particular embodiment, two or more microbubble generation systems are stacked on top of one another to form a reactor stack. In a particular embodiment, a single gas stream is split and provided to each of the two or more microbubble generation systems that form the reactor stack. In a particular embodiment, the two or microbubble generation systems that form the reactor stack are connected to one another via a mechanical support structure.

According to a second aspect, the invention provides a method of microbubble generation comprising:
 a. sparging gas into a column containing a liquid via a gas sparger to form gas bubbles; and
 b. introducing a liquid to the column via a perforated plate positioned above the gas sparger to create a liquid jet such that the liquid jet contacts the bubbles and produces microbubbles.

The liquid introduced may be the same liquid as is already present in the column, or may be a different liquid. The liquid jets break up bubbles formed from sparging of gas into the liquid contained within the column.

In a particular embodiment, the liquid jet contacts a foam layer formed from a mass of bubbles on the surface of the liquid contained within the column.

In a particular embodiment, the top of the foam layer is maintained at the level of the perforated plate.

In a particular embodiment, the diameter of the pores in the perforated plate is such that for a given total volumetric liquid flow, a desired liquid jet velocity can be maintained. Preferably, the pores are from about 0.1 to about 0.5 mm. Preferably about 0.2 mm diameter.

In a particular embodiment, the liquid contained in the column and/or the liquid stream introduced to the column contains one or more surface active species. In particular embodiments, these surface active species comprise proteins, peptides, ionic or non-ionic surfactants, bio-surfactants, hydrophobic or amphiphilic particles including but not limited to cells of certain microorganisms.

In a particular embodiment, the bubble generated from a sparger with a pore size of 0.5 mm has a diameter of approximately 3 mm.

In a particular embodiment, the microbubble diameter generated following contact of the liquid jet with the one or more bubbles is about 200 to about 10 μm.

In a particular embodiment, the liquid is introduced to the column at a particular liquid inlet flow rate, the gas is sparged at a particular sparging flow rate and said flow rates are controlled such that the rate of formation of bubbles is equal to the rate at which the bubbles are broken into microbubbles by the liquid jets.

In a particular embodiment, the method further comprises the extraction of a microbubble product from the column via a liquid outlet. Preferably, the liquid outlet is positioned at a level above the level of the sparger to enable bubbles to be formed in a liquid layer free from microbubbles.

In a particular embodiment, the liquid to gas volume ratio of the microbubble product extracted from the column is controlled by adjusting the rate at which gas is sparged and the rate at which liquid is introduced to the column.

In a particular embodiment, the size of the bubbles in the microbubble product is controlled by adjusting the initial bubble size and the jet velocity. The jet velocity is controlled by the volumetric liquid flow rate through the porous plate, pore number and pore diameter. The initial bubble size is controlled by adjusting the sparger pore diameter and the gas sparging flow rate.

In a particular embodiment, the total mass flux of the gas flows in both directions are equal to each other when the microbubble generator is in continuous operation.

In a particular embodiment, the gas pressure in the column is released via a gas relief valve. Preferably, the gas relief valve is located in the column at a level substantially adjacent and below the level of the perforated plate.

In a particular embodiment, the method comprises the use of a microbubble generation system as described in the first aspect.

In a particular embodiment, the method of microbubble generation is used in conjunction with a method of gas fermentation to produce one or more fermentation products. In a particular embodiment, the fermentation is carried out inside a bioreactor wherein the bioreactor may be the column as herein described, or one or more separate bioreactor vessels.

In a particular embodiment, the method comprises the step of mass transfer from the gaseous substrate to one or more micro-organisms in a fermentation broth containing the microbubble product.

In a particular embodiment, the fermentation broth comprises a culture of one or more carboxydotrophic microorganisms capable of producing one or more products by fermentation of a microbubble product containing CO.

In a particular embodiment, at least a portion of the broth from the bioreactor is passed to a primary gas-liquid separator. In particular embodiments, at least a portion of a substantially gas component of the broth is separated by the primary gas-liquid separator and is passed to the column via a compressor/blower and the gas sparger. In a further embodiment, at least a portion of a substantially gas component of the broth is removed from the system by the primary gas-liquid separator.

In a particular embodiment, the primary gas-liquid separator adds an anti-foam spray to the portion of the broth.

In a particular embodiment, the primary gas-liquid separator passes at least a portion of the broth to a secondary gas-liquid separator, and/or passes at least a portion of the broth to a product withdrawal outlet for product extraction.

In a particular embodiment, fresh media is added to the broth in the secondary gas-liquid separator before at least a portion of the broth is passed to the liquid inlet on the column, preferably via a liquid pump. In a particular embodiment, at least a portion of gas separated from the broth in the secondary gas-liquid separator is passed to a gas outlet for removal from the system.

In a particular embodiment, the broth received from the primary gas-liquid separator is returned directly to the liquid inlet on the column, preferably via a liquid pump.

In a particular embodiment, the method of microbubble generation is used in conjunction with a method of foam fractionation to yield one or more surface active species.

In a particular embodiment, at least a portion of a microbubble product is passed from the column to a foam/liquid separator for fractionation.

In a particular embodiment, the foam/liquid separator passes at least a portion of a substantially liquid fraction to a liquid inlet on the column, preferably via a liquid pump.

In a particular embodiment, the foam/liquid separator passes at least a portion of a substantially foam fraction to a de-foaming tank. When a surface active species is present in the microbubble product, the foam fraction will contain a higher concentration of the substance.

In a particular embodiment, an anti-foam spray is applied to the substantially foam fraction to yield a foamate product which is removed from the system for further processing.

In a particular embodiment, the method comprises a microbubble gas absorption system wherein a first gas component comprising one or more gases is separated from a second gas component comprising one or more gases, wherein the first gas component is substantially soluble in the liquid and the second gas component is less soluble or substantially insoluble in the liquid.

In a particular embodiment, a multi-component gas stream is sparged into the column containing a liquid to produce a microbubble product which is then passed from the column to a gas-liquid separator.

In a particular embodiment, the gas-liquid separator removes at least a portion of the less soluble or substantially insoluble gas component from the microbubble product to yield a liquid component containing a dissolved substantially soluble gas component.

In a particular embodiment, the liquid component is removed from the system and may be subjected to an effervescence technique known to one of skill in the art to enable collection of the separated gas.

In a particular embodiment, the first gas component comprises $CO_2$ and the liquid comprises monoethanolamine or water.

In a third aspect, the invention provides a product produced by the method of the second aspect.

In a particular embodiment, the product is a fermentation product selected from the group consisting of ethanol, butanol, 2,3-butanediol, acetone, isopropanol, acetic acid, lactic acid, phosphoric acid and biomass.

In a particular embodiment, the product is a surface active species separated by a foam fractionation method. Preferably, the species is selected from the group consisting of proteins, peptides, ionic or non-ionic surfactants or bio-surfactants.

Further aspects of the invention, which should be considered in all its novel aspects, will become apparent to those skilled in the art upon reading the following description which provides at least one example of a practical application of the invention.

BRIEF DESCRIPTION OF THE DRAWINGS

Embodiments of the invention will now be described, by way of example only, with reference to the accompanying drawings in which.

DETAILED DESCRIPTION OF PREFERRED EMBODIMENTS

Definitions

Figure 1:
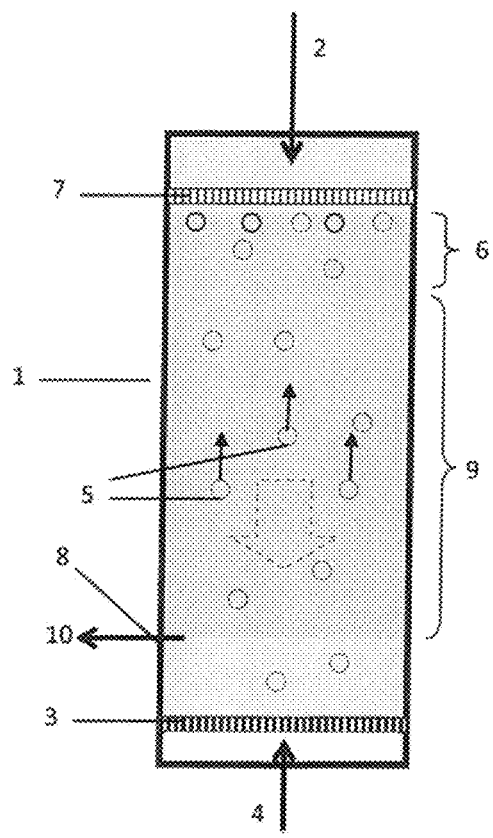
FIG. 1 is a schematic diagram of a microbubble generator of the invention.

A "sparger" comprises a device to introduce gas into a liquid to agitate it or to dissolve the gas in the liquid. In a particular embodiment, the sparger may be a perforated plate, sintered glass, sintered steel, porous rubber pipe, porous metal pipe, porous ceramic or stainless steel. The sparger may be of various grades (porosities) to provide a specific sized "bubble".

A "column" is a vessel where one or more gas and liquid streams are introduced for bubble generation and microbubble generation, and for subsequent gas-liquid contacting, gas-absorption, bio/chemical reaction, surface active material adsorption. In a column the gas and liquid phases flow in the vertical direction. In a column larger bubbles of which the buoyancy force is larger than the drag force imparted by the liquid rise upwards, whilst smaller bubbles of which the buoyancy force is less than or equal to the drag force imparted by the liquid flow downwards with the liquid. A column is not restricted to any specific aspect (height to diameter) ratio. A column is not restricted to any specific material and can be constructed from any material suitable to the process such as but not limited to stainless steel or PVC. A column may contain internal components such as but not limited to one or more static mixers that are common in bio/chemical engineering processing. A column may consist of external or internal heating or cooling facilities such as but not limited to water jackets.—"perforated plate" comprises a plate or similar arrangement designed to facilitate the introduction of liquid to the column in the form of multiple liquid jets (referred to herein as a "liquid jets"). Typically, the perforated plate will have pores evenly distributed across the plate that allow the flow of liquid from one side of the plate to the other. In alternative embodiments, the plate may comprise one or more nozzles adapted to generate liquid jets which flow into the column. The plate may contain channels in any distribution or alignment where such channels are adapted to receive liquid and facilitate flow through into the column. The plate can be made of stainless steel with a predefined number of laser-burnt holes or "pores". The specific pore size depends on the application that the microbubble generation system is used for. In a particular embodiment, the pore size is about 130 μm diameter. Preferably, the pores are arranged in an offset row arrangement so that each pore in a row is equidistant to the two pores in the row immediately above and below said pore. A perforated plated of the same or a different porosity can be used as a gas sparger.

As referred to herein "foam" is a mass of bubbles of gas in a matrix of liquid film. The volumetric liquid fraction of a foam is preferably less than 10%, preferably less than 5%, preferably less than 2%.

A "foam/liquid separator" is an apparatus designed to separate foam from liquid by allowing the micro-bubble containing gas-liquid mixture to settle for a certain amount of time (the residence time), during which period, the gas bubbles rise and accumulate at the liquid surface to form a foam layer and the interstitial liquid in the foam drains back to the liquid pool beneath the foam layer under gravity. Examples of foam/liquid separators will be known to one of skill in the art, however, by way of example, a foam/liquid separator may be a vertical vessel where the gas-liquid mixture containing micro-bubbles is continuously introduced into the vessel through a port in the middle section. Foam is continuously extracted from a port located at the top of the vessel and the liquid separated from the foam is continuously withdrawn from a port located at the bottom of the vessel. A liquid level control valve may be used to maintain the foam/liquid interface inside the vessel by adjusting the withdrawal rate of the liquid.

As referred to herein a "de-foaming tank" is a vessel where the foam is completely collapsed to yield a liquid form (the foamate) concentrated in surface active materials. The gas originally encapsulated in the bubbles is releases and vented. By way of example, a de-foaming tank may be a stainless steel vessel where foam is introduced into the vessel via appropriate pipe work and a suitable de-foamer (anti-foam agent) is sprayed on the foam to cause the bubbles in the foam to collapse. Mechanical stirrer may be used to aid the distribution of the de-foamer within the bulk of the foam in the tank. In continuous mode of operation, foam is fed into the vessel continuously and the foamate is withdrawn continuously.

A "gas/foam separator" is an apparatus designed to separate gas from foam by. Examples of gas/foam separators will be known to one of skill in the art. The bubble 'classification zone' is a section in the micro-bubble column of this invention where there are simultaneous ascending of larger bubbles and descending of micro-bubbles based on the differences in bubble size, thus differences in the relative magnitudes of drag force and buoyancy force imparted on the bubbles.

A "gas/liquid separator" is an apparatus designed to separate gas from liquid by allowing the gas-liquid mixture to settle for a certain time (the residence time) during which period a substantially liquid fraction settles to the bottom of the vessel, where it is withdrawn. The gas released from the gas-liquid mixture accumulates in the upper portion of the vessel, where it is vented or recycled. In particular cases where the liquid phase contains one or more surface active materials and the gas is encapsulated in stable bubbles, a de-foamer (anti-foam) is used to collapse the bubbles thus to release the gas from the bubbles. In particular cases where the gas-liquid mixture is pressurized and one or more gas components are dissolved in the liquid, the gas/liquid separator vessel is capable of depressurising the gas-liquid mixture thus to release the gas from the liquid for subsequent separation. Examples of gas/liquid separators will be known to one of skill in the art, however, by way of example, a gas/liquid separator may be a vertical vessel constructed stainless steel and equipped with appropriate pipe work, ports and pumps, where the gas-liquid mixture is introduced into the vessel via a port located in the middle section, the liquid is withdrawn from the bottom and the gas is extracted via a port at the top. In another example the gas-liquid separator is raised to a higher elevation where the pressure is lower than the upstream vessel where the gas-liquid mixture is from to cause the dissolved gas to be released from the liquid and subsequently separated. As referred to herein an "anti-foam spray" refers to a dynamic collection of tiny anti-foam (de-foamer) droplets dispersed in a gas generated from a sprayer of an appropriate type, such as a spray nozzle. In particular embodiments, the anti-foam spray comprises a spray nozzle through which a pressurized de-foamer is dispersed onto the surface of a foam layer in the form of tiny droplets and the foam is subsequently collapsed due to the action of the anti-foam (de-foamer).

As referred to herein "surface active species" refers to compounds that lower the surface tension of a liquid and stabilise a gas-liquid dispersion such as foam or microbubbles. In particular embodiments, the surface active species comprises proteins, peptides, ionic or non-ionic surfactants or bio-surfactants. The surface active species can be produced naturally through the activity of the microorganisms in a fermentation process, or they can be added to a solution artificially.

As referred to herein, a "microbubble" is a bubble of gas with a diameter of about 200 to about 10 μm.

As referred to herein, a "microbubble product" is a liquid/gas mixture containing microbubbles.

As referred to herein, a "fermentation broth" is a culture medium comprising at least a nutrient media and bacterial cells.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$, for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of materials to a fermentation reaction should be understood to include addition to either or both of these reactors.

The term "bioreactor" (or "column" where the column is also the bioreactor) referred to herein includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble/micro-bubble Column, Gas Lift Fermenter, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

As referred to herein, a "stack of reactors" or "reactor stack" is a configuration of multiple microbubble reactors, wherein one reactor is placed on top of another with appropriate ducts, pumps, pipes, fittings and a mechanical supporting structure. A stack of reactors increases the throughput of a reactor system without significantly increasing the demand for land area.

The inventors have developed a microbubble generation system with increased efficiency and flexibility compared to known systems.

The invention makes use of multiple liquid jets to break large bubbles into microbubbles in a column. Large bubbles are initially generated by sparging gas with a gas sparger at the bottom or a lower section of the column. These large bubbles migrate upwards through the liquid to a foam layer sitting atop the liquid. Liquid jets are formed by pumping liquid through a perforated plate into the foam layer. The jets have the effect of breaking the foam bubbles into smaller microbubbles which are washed down the column by the liquid flow. Larger bubbles are retained in the foam layer to be broken into smaller bubbles or if they are washed down, they re-migrate upwards. The microbubble product comprising the liquid/bubble mixture is removed from the column via a liquid outlet and may be used for other applications as will be known by those of skill in the art or may be described herein.

Generally, it is desirable to produce the smallest bubble possible for a given energy consumption. The invention provides advantages over known systems in that it has increased energy efficiency for generation of a microbubble product with a particular bubble size at a desired gas/liquid ratio. This is because gas is introduced by direct sparging in the form of large gas bubbles, rather than 'entrainment' which requires high-speed relative motion between the liquid and the gas phases. Microbubbles are generated by the invention by breaking big gas bubbles, rather than by breaking the liquid surface.

Furthermore, the microbubble generation system of the invention can be operated at a wide range of throughputs at which the microbubble product size can be kept constant. The bubble size is dependent on the jet velocity and the residence time of the gas phase in the column. For a given gas sparging rate, when the liquid velocity is reduced, the residence time of gas is autogenously increased.

The current invention does not have any specific requirement of jet velocity and it may vary based on the requirements of the specific application. The turbulence produced by the present invention is minimal compared to known systems (such as the Jameson cell). This has an advantage in terms of increased energy efficiency and a less harsh environment (in terms of shear and turbulence) for proteins or microorganisms present in the liquid.

An additional advantage of the invention is that the microbubble generation occurs in a single vessel (column) with much reduced number of moving parts compared to known systems. This reduces cost, complexity, maintenance requirements and assists with maintaining continuous operation.

In a particular embodiment shown in FIG. 1, a column 1 is initially at least partially filled via a liquid inlet 2 with a liquid containing one or more surface active species, such as but not limited to proteins, peptides, ionic or non-ionic surfactants or bio-surfactants to a desired level. The column may also contain one or more further liquid inlets or liquid outlets at any appropriate position on the column to facilitate filling and emptying of the liquid from the column. The column 1 comprises a sparger 3 connected to a gas inlet 4 which sparges gas into the liquid. The sparger is located so that the bubbles it generates 5 migrate upwards through the classification zone 9 by way of their buoyancy towards the foam layer 6 of the column 1. The bubble diameter generated from the sparger 3 has to be large enough to have a certain rising velocity so that it is not pushed down by the force of the liquid jets flowing through the perforated plate 7.

The bubbles generated from the sparger migrate to the top of the liquid and form a foam layer 6. Initially, the thickness of the foam layer grows as gas sparging proceeds but it is maintained at a constant thickness in a continuous mode of operation. The top of the column 1 contains a perforated plate 7 through which the liquid can be passed to form multiple liquid jets inside the column. The perforated plate is situated above the gas sparger to enable the liquid jets to contact the foam layer produced by the sparger. It will be appreciated by a skilled person that the perforated plate is not required to be situated immediately above the sparger; it may be offset or in any suitable arrangement that enables the introduction of liquid jets to the foam layer. Additionally, the column may be aligned off-vertical depending on the requirements of the particular application. Preferably, the top of the foam layer 6 is maintained at the level of the perforated plate 7. The diameter of the pores should be such that for a given total volumetric liquid flow, a desired liquid jet velocity can be obtained. The liquid jet produced by the flow of the liquid through the porous plate punches the surface of the foam, breaking the bubbles in the foam layer 6 into microbubbles.

Depending on the desired application, the micro-bubble can be of a diameter of less than 200 µm, preferably less than 150 µm, preferably less than 100 µm, preferably less than 60 µm. The microbubbles travel downward through the classification zone 9 inside the column with the liquid, whilst at the same time new bubbles are generated at the bottom or a lower section of the column via the gas sparger. The liquid inlet flow rate and gas inlet flow rate are controlled so that the rate at which new bubbles are generated is equal to the rate at which the bubbles at the top of the foam layer are broken into micro-bubbles.

The column further comprises a liquid outlet 8 where the microbubble product 10 exits the column. For a straight column without any expansion or contraction in width/diameter, a distance between the liquid outlet 8 and the sparger 3 is desirable so that bubbles are generated in a zone apart from the classification zone and substantially free from microbubbles. If the bubbles are sparged directly into the classification zone 9 the bubble size given by the sparger is harder to control due to the downward velocity of liquid. Very large bubbles and inconsistent bubble size can result.

The liquid to gas volume ratio of the microbubble product 10 coming out of the column is controlled by the inlet gas flow rate and the inlet liquid flow rate. The size of the bubbles in the microbubble product is controlled by adjusting the initial bubble size and the jet velocity. The jet velocity is controlled by the volumetric liquid flow rate and pore number and pore diameter. The initial bubble size is controlled by adjusting the sparger hole diameter and the gas sparging flow rate.

The invention is characterised by a simultaneous up flow of larger bubbles and downflow of micro-bubbles inside the column. For an inert gas, the total mass flux of the gas flows in both directions are equal to each other when the microbubble generator is in continuous operation. For a reactive gas the mass flux of inlet gas equals to the mass flux of downflow gas, plus the mass flux of gas consumed by the reaction. If the gas flow exceeds what the liquid jets can break, a gas layer will be formed beneath the perforated plate. To facilitate gas relief in this scenario, the column may further comprise a gas relief valve to release the gas. The pressure inside the column may be controlled by an optional pressure release valve connected to the liquid outlet 8.

Enrichment and Extraction of Surface Active Materials

In a particular embodiment, the microbubble generation system is part of a microbubble foam fractionation process and apparatus for enriching and extracting surface active species (such as proteins, peptides, ionic or non-ionic surfactants or bio-surfactants) from a solution. When a surface active species is present in the microbubble product, the foam fraction will contain a higher concentration of the substance and so is desirable for further processing including extraction and/or purification, transport, storage.

Figure 2:
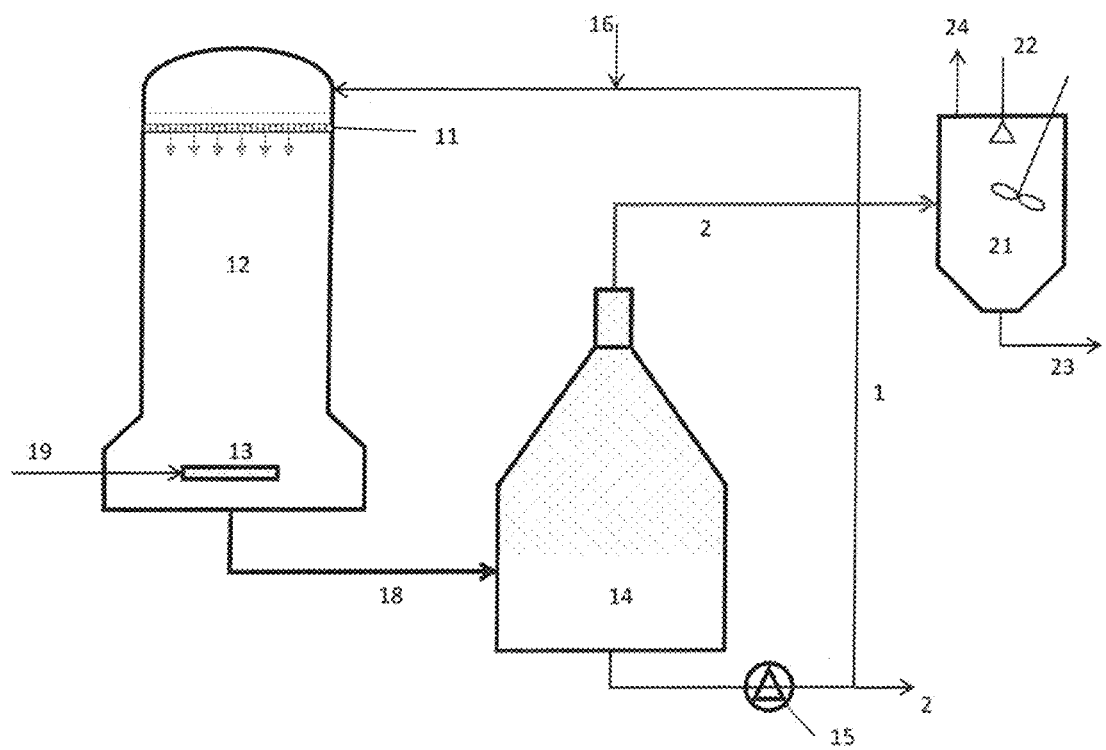
FIG. 2 shows an embodiment of the invention used for micro-bubble foam fractionation.

An embodiment is shown in FIG. 2 wherein a microbubble product is produced by sparging a gas from a sparger 13 received from a gas inlet 19 and a liquid jet is produced by passing a liquid through a perforated plate 11. At least a portion of the microbubble product 18 is passed from the column 12 to a foam/liquid separator 14 for fractionation. The foam/liquid separator passes at least a portion of a substantially liquid fraction 17 to a liquid inlet on the column, preferably via a liquid pump 15. Before being returned to the column 12, the substantially liquid fraction may be supplemented with fresh liquid feed 16. At least a portion of the substantially liquid fraction may be removed from the system by way of a liquid outlet 25. The foam/liquid separator passes at least a portion of a substantially foam fraction 20 to a de-foaming tank 21. An anti-foam spray 22 is applied to the substantially foam fraction to yield a foamate product 23 which is removed from the system for further processing and extraction of the desirable surface active species. Any excess gas may be removed from the de-foaming tank via a gas outlet 24.

In a particular embodiment, the microbubble foam fractionation process may be used to extract proteins from dairy feedstock. The proteins adsorb to the surface of microbubbles in a foam which can be removed and collapsed to yield an enriched product. If the bubbles are very small then there is a greater specific surface area onto which the proteins can adsorb. Existing methods of small bubble generation are energy inefficient and create zones of very high shear stress which can denature the protein. In addition, because of the high specific surface area, the microbubbles produced by the present invention are excellent for interfacial adsorption.

In a particular embodiment, the microbubble fractionation process may be used to remove the protein from a waste stream, for example from a wastewater treatment operation so as to reduce the biological oxygen demand (BOD). This would have particular utility for treating waste streams prior to release into the environment or further treatment. In this case, the invention is expected to remove a substantial portion of the protein from the feed stream. In particular embodiments, the portion of surface active species removed from the solution is greater than 50%, 60%, 70%, 80% or 90% of the total amount of species in the solution.

Microbubble Gas Fermentation System

In a particular embodiment, the microbubble generation system is part of a gas fermentation system. A particular gas fermentation system according to the invention comprises a bioreactor containing a microorganism and a fermentation broth. The microorganism utilises gases dissolved in the broth to produce at least one product such as ethanol or 2,3-butanediol. The bioreactor of the system may be the column previously described as being part of the microbubble generation system, or may be a separate vessel.

In typical gas fermentations, especially using relatively insoluble gas species such as $O_2$ and CO, one of the major limitations is the amount of gas that can be dissolved in the fermentation substrate, and the rate at which it can be dissolved. The invention provides an improved method of mass transfer from the gaseous substrate to one or more microorganisms in a fermentation broth containing the microbubble product.

Figure 3:
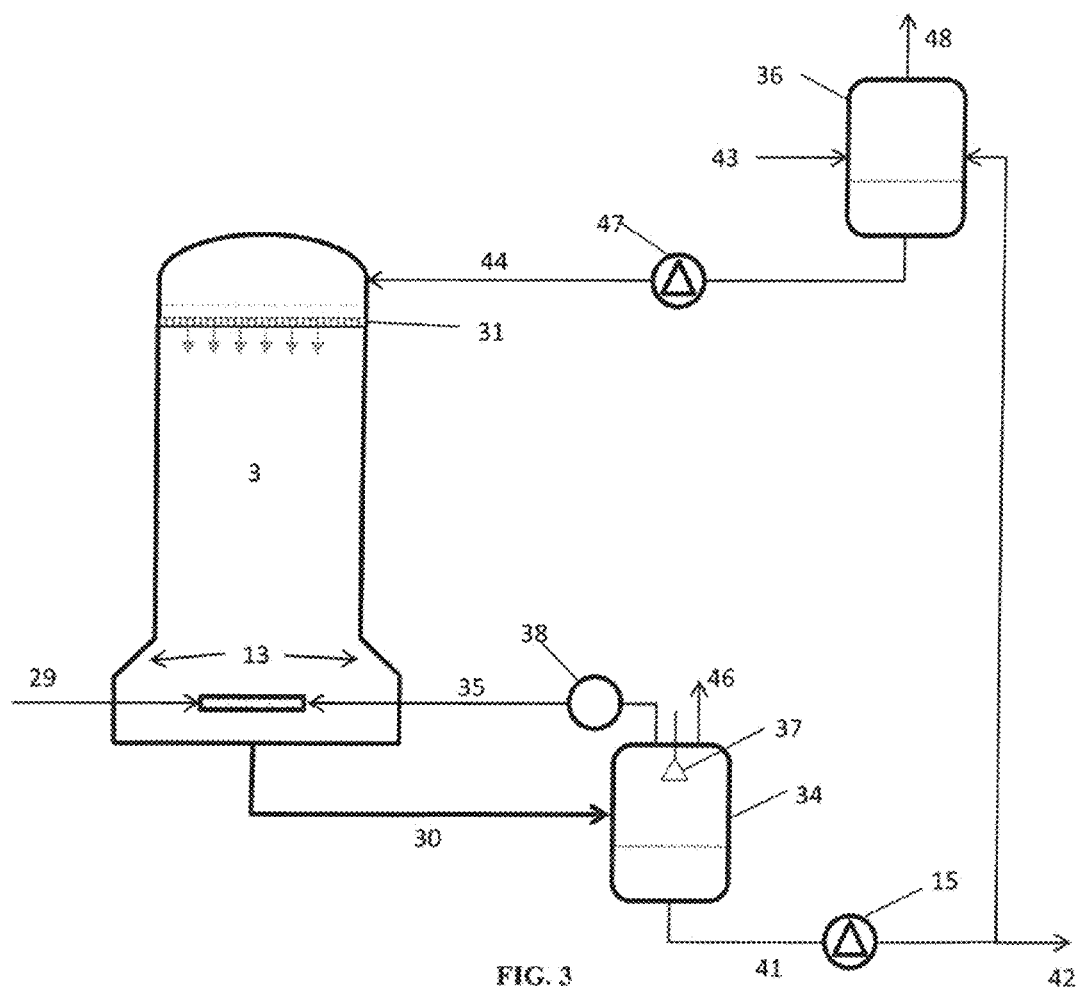
FIG. 3 shows an embodiment of the invention used for microbubble generation in a gas fermentation system.

In a particular embodiment shown in FIG. 3, the liquid is introduced to the column 32 via the perforated plate 31 to form liquid jets. In this particular embodiment, the column is also the bioreactor. Gas 29 is sparged into the liquid to produce foam which is broken down into a microbubble product 30 which is in turn passed to a primary gas-liquid separator 34. A substantially gas component of the broth is separated by the primary gas-liquid separator and is passed 35 to the column via a compressor/blower 38 and the gas sparger. A portion of a substantially gas component of the broth may be removed from the system 46 by the primary gas-liquid separator 34. The primary gas-liquid separator may add an antifoam spray 37 to the portion of the broth contained therein.

The primary gas-liquid separator passes 41 at least a portion of the broth to a secondary gas-liquid separator 36, and/or passes at least a portion of the broth to a product withdrawal outlet 42 for product extraction. Fresh media 43 is added to the broth in the secondary gas-liquid separator 36 before at least a portion of the broth 44 with low gas content is passed to the liquid inlet on the column, preferably via a liquid pump 47. At least a portion of gas separated from the broth in the secondary gas-liquid separator is passed to a further gas outlet 48 for removal from the system.

In the embodiment in FIGS. 2 and 3, it can be seen that the column contains an expansion section (labelled 13 on FIG. 3) at the bottom of the column. In this section, the liquid velocity is low and the bubbles generated by the sparger can form and rise more easily. In this embodiment, the liquid outlet is not located on the side of the column as in FIG. 1 and may be located at other positions, such as in the base of the column.

The microbubble product is typically fed into (or produced in) the bioreactor. The microbubble product has the advantage that the high surface area of gas to liquid enhances the absorption of the gas by the liquid. When using gases with a low solubility such as CO or $O_2$, it is desirable to maximise gas absorption to facilitate microorganism growth and production.

Extraction of Gases from a Gas Stream

In a particular embodiment, the method comprises a microbubble gas absorption system wherein a first gas component comprising one or more gases is separated from a second gas component comprising one or more gases, wherein the first gas component is substantially soluble in the liquid and the second gas component is less soluble or substantially insoluble in the liquid.

In this embodiment, the system is used to separate a gas component from a multi-component gas stream by dissolution of the gas component in the liquid. This embodiment has particular utility for removal of gases from a multi-component gas mixture where the gas to be dissolved exhibits high solubility in a liquid compared to the other gases to be retained in the gas phase. Liquids may comprise any suitable solute such as water or monoethanolamine. In a particular embodiment, it may be desirable to recover $CO_2$ from a waste gas stream containing a number of other gases. To maximise the recovery of the $CO_2$, the microbubble generator of the invention is used to produce microbubbles in a $CO_2$ absorbing liquid. The liquid (with dissolved $CO_2$) is then separated from the gaseous component of the mixture and the $CO_2$ is recovered by standard effervescence techniques such as lowering pressure, increasing temperature or agitation.

Methods of Production

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and the production of products to occur, in addition to the CO-containing substrate gas, a suitable liquid nutrient medium will need to be fed to the bioreactor.

In particular embodiments of the method aspects, the fermentation occurs in an aqueous culture medium. In particular embodiments of the method aspects, the fermentation of the substrate takes place in a bioreactor.

The substrate and media may be fed to the bioreactor in a continuous, batch or batch fed fashion. A nutrient medium will contain vitamins and minerals sufficient to permit growth of the micro-organism used. Anaerobic media suitable for fermentation using CO are known in the art. For example, suitable media are described Biebel (2001). In one embodiment of the invention the media is as described in the Examples section herein after.

The fermentation should desirably be carried out under appropriate fermentation conditions for the production of the biofuel to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of fermentation. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that one or more product is consumed by the culture.

The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Products may be recovered from the fermentation broth by methods known in the art, such as fractional distillation or evaporation, pervaporation, gas stripping and extractive fermentation, including for example, liquid-liquid extraction. Products may also diffuse or secrete into media, from which they can extracted by phase separation.

In certain preferred embodiments of the invention, products are recovered from the fermentation broth by continuously removing a portion of the broth from the bioreactor, separating microbial cells from the broth (conveniently by filtration), and recovering the product from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

In one particular embodiment, the carboxydotrophic microorganism used in a fermentation reaction of the invention is selected from the group of carboxydotrophic acetogenic bacteria comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kiuvi.*

In one particular embodiment, the microorganism is selected from the cluster of ethanologenic, acetogenic *Clostridia* comprising the species *C. autoethanogenum, C. ljungdahlii,* and *C. ragsdalei* and related isolates. These include but are not limited to strains *C. autoethanogenum* JAI-1$^T$ (DSM10061) (Abrini, Naveau, and Nyns 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, and Yang 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), *C. ragsdalei* P11$^T$ (ATCC BAA-622) (WO 2008/028055), related isolates such as "*C. coskatii*" (US20110229947) and "*Clostridium* sp." (Tyurin and Kiriukhin 2012), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species (WO 2008/028055).

All species of this cluster have a similar morphology and size (logarithmic growing cells are between 0.5-0.7×3-5 μm), are mesophilic (optimal growth temperature between 30-37° C.) and strictly anaerobe (Abrini, Naveau, and Nyns 1994; Tanner, Miller, and Yang 1993) (WO2008/028055). Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions (Abrini, Naveau, and Nyns 1994; Köpke et al. 2011; Tanner, Miller, and Yang 1993) (WO 2008/028055). Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotroph to certain vitamins (e.g. thiamine, biotin) while others were not. The organization and number of Wood-Ljungdahl pathway genes, responsible for gas uptake, has been found to be the same in all species, despite differences in nucleic and amino acid sequences (Köpke et al. 2011).

In one embodiment the parental microorganism is *Clostridium autoethanogenum* or *Clostridium ljungdahlii*. In one particular embodiment, the microorganism is *Clostridium autoethanogenum* DSM23693 a derivate of strain DSM10061. *C. autoethanogenum*. In another particular embodiment, the microorganism is *Clostridium ljungdahlii* DSM13528 (or ATCC55383).

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Wherein the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the scope of the invention.

EXAMPLES

Example 1

Bench Scale Foam Fractionator

Materials and Methods

The main column has an internal diameter of 90 mm and a height of 600 mm. The coarse gas sparger at the bottom of the column is a pipe-with-holes type of sparger. The pore diameter of this sparger is about 0.5 mm. The bubble size generated from this coarse gas sparger is around 3 mm.

Figure 4:
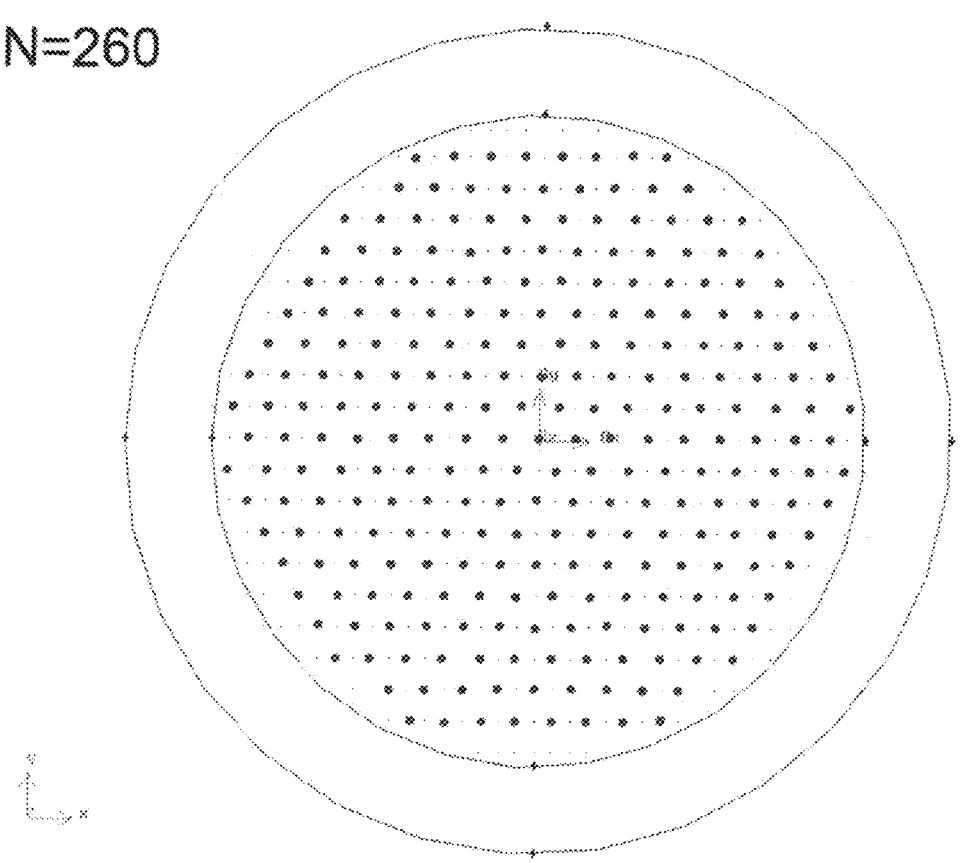
FIG. 4 shows a pore arrangement on a porous plate used in an embodiment of the invention.

An example of the porous plate used for generating the liquid jets is shown in FIG. 4. The plate has 260 pores with 0.2 mm average diameter arranged in triangle pattern with pore-to-pore distance of 5 mm. The plate is made of stainless steel with laser-punched pores.

The experiment was carried out using a model solution, which was 0.1 g/L SDS in distilled water. The Liquid volumetric flow rate, $Q_L$, was 18.45 mL/s. This gives a jet velocity, $v_j$, of 2.3 m/s by the relationship $$Q_L = N \times \frac{\pi}{4} \times d^2 \times v_j \quad (1)$$

where N is the total number of pores on the porous plate and d is the diameter of the pores.

The superficial liquid velocity, $v_L$, in the main column is calculated by $$v_L = Q_L/A_C \quad (2)$$

where $A_C$ is the cross sectional area of the column. In this example, $A_C = 6362$ mm² thus $v_L = 2.9$ mm/s.

For the same liquid flow rate, the gas flow rate can vary depending on the actual application. In one example, the gas volumetric flow rate was 27 mL/s measured at the outlet (the column was operated at atmosphere pressure the column height is small thus compression of gas within the column is negligible).

By conservation of volume, the product stream has to have a gas to liquid fraction of 27:18.45, i.e., the liquid fraction is $$\varepsilon_L = \frac{18.45}{18.45 + 27} = 0.4.$$

The true liquid velocity relative to the stationary column thus is $$u_L = \frac{v_L}{\varepsilon_L} = \frac{2.9}{0.4} = 7.5 \text{ mm/s}.$$

Figure 5:
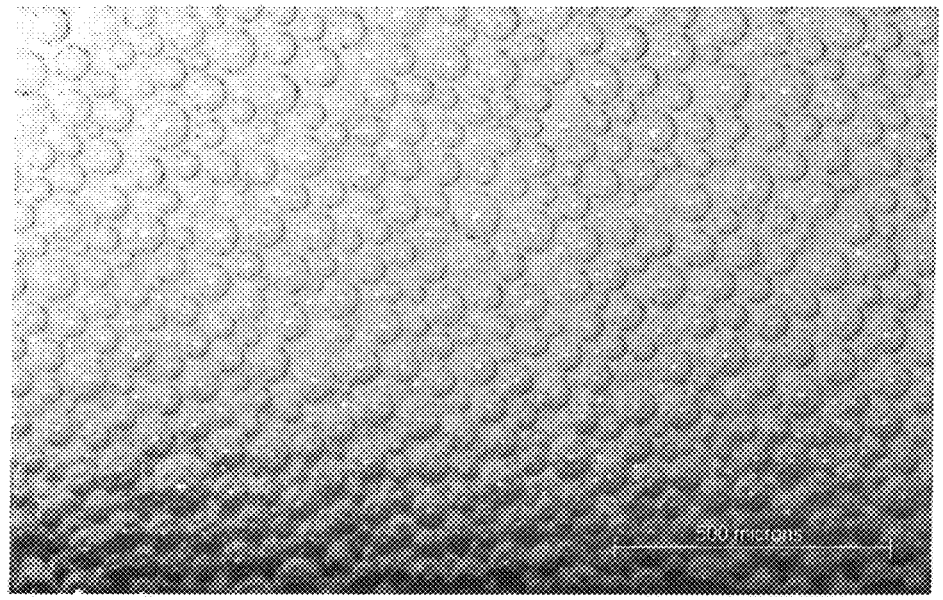
FIG. 5 shows an image of microbubbles at a level substantially adjacent and below the perforated plate within the column of the micro-bubble generator.
Figure 6:
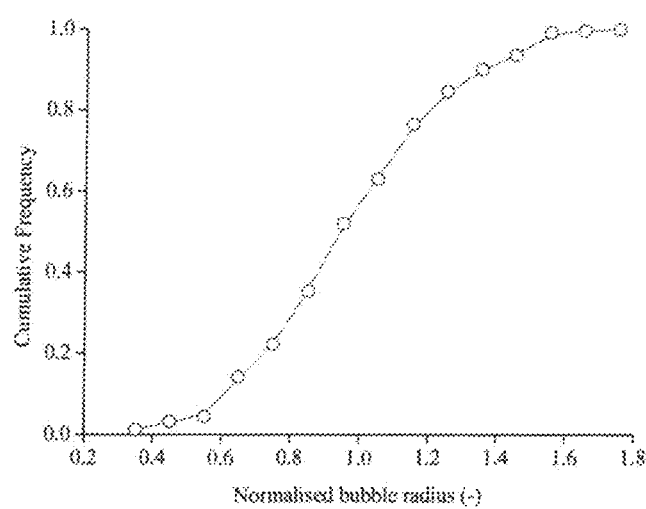
FIG. 6 shows cumulative bubble size distribution and illustrates that the average bubble size is about half of the maximum bubble size.

This means that only those bubbles that have a terminal velocity, $v_t$, smaller than 7.25 mm/s can be carried out by the downwards flowing liquid. Using the Stokes' equation (Wallis G. B., *One-dimensional Two-phase Flow*, 1969), i.e.

$$v_t = \frac{1}{18} \frac{d_b^2 g (\rho_L - \rho_G)}{\mu_L} \quad (3)$$

one can estimate the maximum bubble diameter, $d_b$, in the product stream. Equation (3) gives that the maximum bubble diameter in the product stream is 0.115 mm, i.e., 115 microns or μm. Note that this is the maximum bubble diameter for this embodiment; it does not mean all the bubbles in the product stream are of this diameter. Photographic measurement (FIG. 5) shows that the average bubble diameter is about 0.06 mm, i.e., 60 microns, which is half of the maximum bubble diameter, as shown in the graph in FIG. 6 which shows cumulative bubble size distribution. There is also a large portion of the bubbles that are even smaller and cannot be seen from the image in FIG. 5.

In a particular embodiment, the operating parameters for an exemplary micro-bubble foam fractionator as shown in FIG. 2 are as follows:

Flow 16, liquid feed, 6 mL/s, surfactant concentration=0.1 g/L

Flow 17, recirculated liquid, 12 mL/s, surfactant concentration 0.01 g/L

Flow 18, gas-liquid mixture, 27 mL/s gas+18 mL/s liquid=45 mL/s mixture

Flow 19, inert gas inlet=27 mL/s

Flow 23, foamate (liquid), 0.54 mL/s, surfactant concentration=0.5 g/L

Flow 20, 27 mL/s gas+0.54 mL/s liquid=27.54 mL/s foam

Flow 24, gas outlet, 27 mL/s

Flow 25, tailing (liquid), 5.46 mL/s, surfactant concentration=0.01 g/L

In this process, the feed solution (6 mL/s, 0.1 g/L surfactant) is converted into a concentrated stream containing 0.5 g/L surfactant (i.e., an enrichment factor of 5) with a 91% yield.

Example 2

A Pilot-Scale Bioreactor

Using the same principles as described in the first example, one can design a larger scale gas-liquid contactor that can be used as a bioreactor. In this example, a bioreactor is designed to achieve 95% conversion of oxygen gas in a 240 L pilot scale reactor. The designed volumetric gas fraction in the micro bubble mixture is 24%.

The main section of the micro-bubble reactor has a diameter of 0.5 m and a height of 1.2 m, with a height to diameter ratio of 2.4. A pump is chosen to give a downward superficial liquid velocity of 0.05 m/s based on the cross-sectional area of the main column. Big bubbles of 2.5 mm diameter are introduced to the bottom of the reactor with a total volumetric gas flow rate of 10 m³/hr, corresponding to a superficial gas velocity of 0.014 m/s. The micro-bubbles generated from this system has a diameter of 120 micron.

The gas holdup in the main column due to the bigger bubbles is 4.5% and gas holdup due to the micro bubbles is 24%. The specific surface area of the gas-liquid mixture, a, due to the big bubbles and micro-bubbles are both calculated by $$a = \frac{6\varepsilon_G}{d_b} \quad (4)$$

where $\varepsilon_G$ is the corresponding gas holdup due to either the big bubbles or micro-bubbles. $d_b$ is the average bubble diameter. Equation 4 shows that the reactor designed above will have a specific surface area of at least $$a = \frac{6 \times 0.24}{0.00012} = 12{,}000 \text{ m}^{-1}.$$

All other things being equal, this reactor will have a volumetric mass transfer coefficient, $k_L a$, at least 10 times as high as a conventional bubble column operated at 20% gas holdup with an average bubble diameter of 1 mm and a specific surface area of 1,200 m$^{-1}$.

This means that to achieve the same productivity, a bioreactor utilising the micro-bubble generator can be 90% smaller than a conventional bubble column reactor or a bubble column reactor under typical operating conditions. This, at least partly, eliminates the requirement of elevated pressure that is typically associated with high energy consumption, and therefore improves the energy efficiency of the system.

Example 3

Reactor Stacks

As demonstrated in the second example, a micro-bubble reactor can be significantly smaller in size than a conventional bubble column reactor. Particularly, a micro-bubble reactor can be significantly shorter in height than conventional bubble column reactors. To better utilise land area, it is pertinent to stack one microbubble reactor on top of another to give an overall height-to-diameter ratio that is comparable to conventional bubble column reactors.

Figure 7:
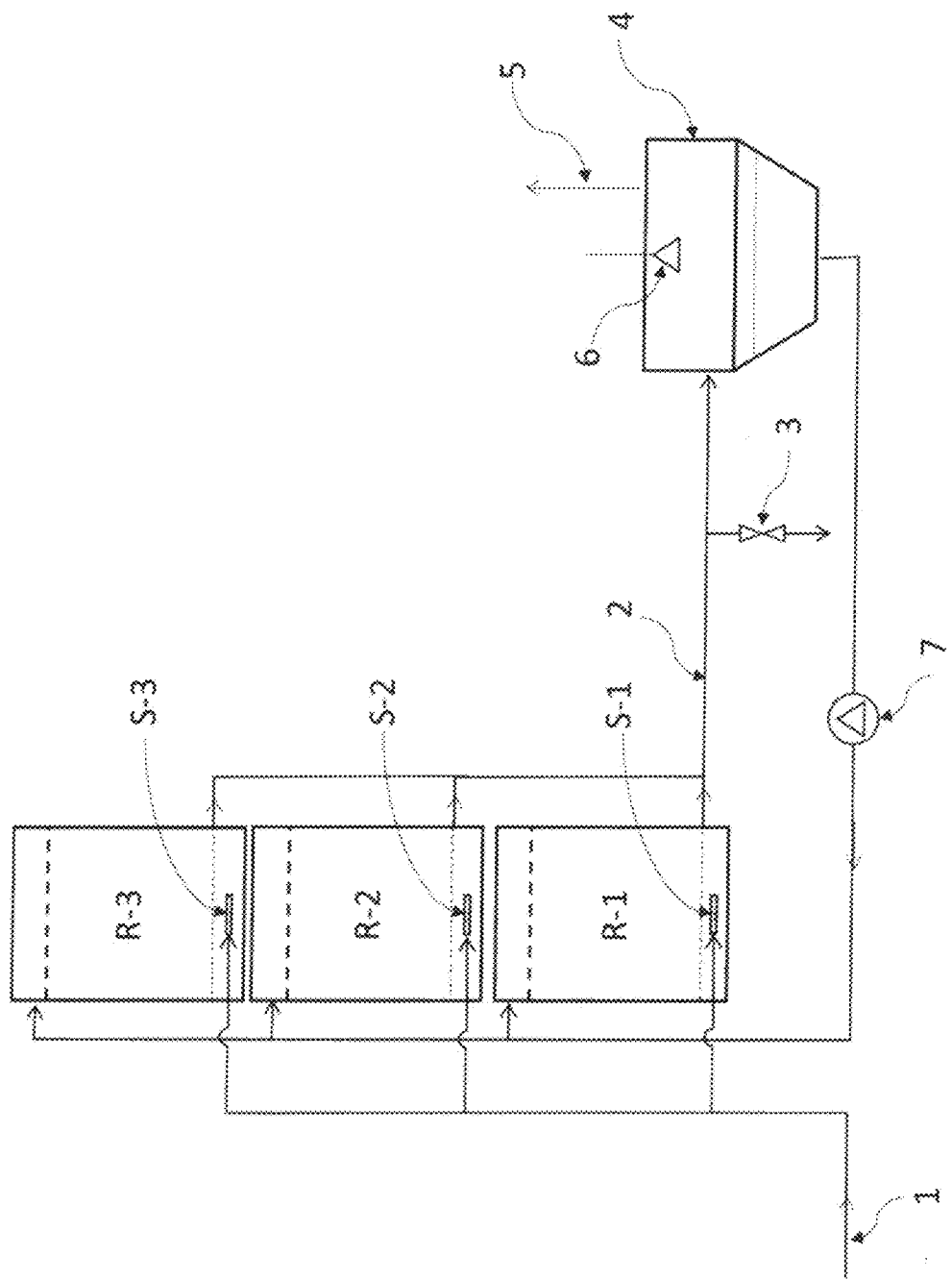
FIG. 7 shows an example of an alternate configuration of multiple micro-bubble reactors where one reactor is placed on top of another to form a stack of reactors.

FIG. 7 shows an example of such configuration where three individual micro-bubble reactors (R-1, R-2, R-3) are placed in a vertical stack. Each of the three individual reactors has the same configuration as that illustrated in FIG. 1. Supporting structures are not included in the drawing for the sake of clarity but should be apparent to those skilled in the art. A gas stream from the main supply 1 is split into each of the three reactors by any appropriate flow and pressure control instruments known to those skilled in the art. The gas flow rates into each reactor can be equal but can also be different to each other. The gas is introduced into each of the reactors in the stack in the form as large bubbles via the corresponding spargers (S-1, S-2, S-3).

The liquid streams containing the micro-bubbles from each individual reactor are collected by a gas-liquid separator 4, upstream wherein a portion of the liquid is withdrawn from the system as the product stream via a flow control valve 3. The gas-liquid separator 4 is equipped with a liquid shower 6 where fresh media that may contain a certain level of anti-foam, or a certain portion of the product stream from another individual reactor or another reactor stack, is sprayed into the gas-liquid separator to aid gas-liquid separation. The exhaust gas leaves the system via a port 5 on the gas-liquid separator. The degassed liquid is required to the micro-bubble generator via a pump 7 and subsequently split into liquid jets for microbubble generation.

The invention claimed is:

1. A method of generating microbubbles comprising:
   (a) sparging gas into a column containing a liquid via a gas sparger to form gas bubbles wherein the gas bubbles migrate upward to the top of the liquid and form a foam layer; and
   (b) introducing additional liquid to the column via an inlet positioned above a perforated plate, said perforated plate positioned above the gas sparger, wherein the foam layer is maintained below the perforated plate, the additional liquid passing downward through the perforated plate to form liquid jets such that the liquid jets contact the bubbles in the foam layer and produce microbubbles entrained in the liquid.

2. The method of claim 1, wherein the perforated plate of step (b) comprises perforations with a diameter from about 0.1 to about 0.5 mm.

3. The method of claim 1, wherein the liquid contained in the column or the additional liquid introduced to the column contains at least one surface active species selected from the group consisting of a protein, a peptide, an ionic surfactant, non-ionic surfactant, and a bio-surfactant.

4. The method of claim 1, wherein the microbubbles produced have a diameter from about 10 to about 200 μm in diameter.

5. The method of claim 1, further comprising passing at least a portion of the microbubble entrained liquid to a foam/liquid separator operated at conditions to produce a separated liquid stream and a separated foam stream.

6. The method of claim 5, further comprising passing at least a portion of the separated liquid stream back to the perforated plate.

7. The method of claim 5, further comprising passing at least a portion of the separated foam stream to a de-foaming tank.

8. The method of claim 1, further comprising passing at least a portion of the microbubble entrained liquid to a gas/liquid separator to produce a separated gas stream and a separated liquid stream.

9. The method of claim 1, further comprising releasing gas pressure from the column via a gas relief valve.

10. The method of claim 1, further comprising providing at least a portion of the microbubble entrained liquid to a culture of at least one microorganism in a fermentation broth to form a second fermentation broth containing the microbubble entrained liquid and anaerobically fermenting the gas in the microbubbles to produce at least one product.

11. The method of claim 10, wherein the microbubbles comprise CO.

12. The method of claim 10, wherein the at least one product is selected from the group consisting of ethanol, butanol, 2,3-butanediol, acetone, isopropanol, acetic acid, lactic acid, and biomass.

13. The method of claim 10, wherein the culture is located inside the column.

14. The method of claim 10, wherein the culture is located in a bioreactor vessel.

15. The method of claim 14, further comprising passing at least a portion of the second fermentation broth from the bioreactor vessel to a primary gas/liquid separator to form a separated gas stream and a separated third fermentation broth stream.

16. The method of claim 15, further comprising passing at least a portion of the separated gas stream back to the column via the gas sparger.

17. The method of claim 15, further comprising passing at least a portion of the separated third fermentation broth stream back to the column via the perforated plate.

18. The method of claim 17, further comprising separating at least one product from the separated third fermentation broth stream prior to passing the third fermentation broth to the column via the perforated plate.

* * * * *